United States Patent
Siddiqi et al.

(10) Patent No.: US 11,969,320 B2
(45) Date of Patent: *Apr. 30, 2024

(54) SUBOCCIPITAL COMPRESSION PAD

(71) Applicants: Fidelis Medical, LLC, Knoxville, TN (US); Arrowhead Neuroscience Foundation, Inc., Colton, CA (US)

(72) Inventors: Javed Siddiqi, Colton, CA (US); Jerry Noel, Colton, CA (US); David Holladay, Knoxville, TN (US)

(73) Assignees: Fidelis Medical, LLC, Knoxville, TN (US); Arrowhead Neuroscience, Colton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/148,626

(22) Filed: Dec. 30, 2022

(65) Prior Publication Data

US 2023/0165725 A1 Jun. 1, 2023

Related U.S. Application Data

(63) Continuation of application No. 16/675,893, filed on Nov. 6, 2019, now Pat. No. 11,571,339.

(60) Provisional application No. 62/756,304, filed on Nov. 6, 2018.

(51) Int. Cl.
*A61F 5/00* (2006.01)
*A61F 13/00* (2006.01)
*A61F 13/12* (2006.01)

(52) U.S. Cl.
CPC ...... *A61F 13/124* (2013.01); *A61F 13/00051* (2013.01); *A61F 2013/0028* (2013.01)

(58) Field of Classification Search
None
See application file for complete search history.

(56) References Cited

U.S. PATENT DOCUMENTS

| | | | |
|---|---|---|---|
| 1,331,042 A | 2/1920 | Andreae | |
| 1,758,764 A | 5/1930 | Roxburg | |
| 3,307,547 A | 3/1967 | Jones | |
| 3,417,749 A | 12/1968 | Bailey | |
| 6,349,416 B1 | 2/2002 | Lampe | |
| 6,554,787 B1 | 4/2003 | Griffin | |
| 8,088,141 B1 | 1/2012 | Reyna | |
| 11,571,339 B2* | 2/2023 | Siddiqi | A61F 13/124 |

(Continued)

FOREIGN PATENT DOCUMENTS

DE 3301532 7/1984

*Primary Examiner* — Kim M Lewis
(74) *Attorney, Agent, or Firm* — Robinson IP Law, PLLC

(57) ABSTRACT

A suboccipital compression pad may include a pad member configured to contact a suboccipital region of a patient. A suboccipital compression pad may include a pair of securing straps extending respectively from opposing ends of the pad member, the pair of securing straps having proximal ends diverging into upper rear straps and lower rear straps to form an open space between the upper rear straps and the lower rear straps such that portions of the upper rear straps are located above ears of the patient and portions of the lower rear straps are located below ears of the patient without covering ears of the patient, wherein one of the upper rear straps and the lower rear straps of the pair of securing straps is configured to be selectively attachable to different locations of a back side of the pad member.

20 Claims, 3 Drawing Sheets

(56) References Cited

U.S. PATENT DOCUMENTS

| | | | |
|---|---|---|---|
| 2002/0007195 A1 | 1/2002 | Wexler | |
| 2005/0251069 A1 | 11/2005 | Mattison | |
| 2010/0331752 A1* | 12/2010 | Cumming | ............... A61F 13/12 607/114 |
| 2014/0237703 A1 | 8/2014 | Tateo | |
| 2016/0243327 A1 | 8/2016 | Kimock | |
| 2018/0344505 A1 | 12/2018 | Gilmer | |

* cited by examiner

SUBOCCIPITAL COMPRESSION PAD

CROSS-REFERENCE TO RELATED APPLICATIONS

This application is a continuation of U.S. application Ser. No. 16/675,893 for a Suboccipital Compression Pad filed on Nov. 6, 2019, which claims priority to U.S. Provisional Patent Application Ser. No. 62/756,304 filed on Nov. 6, 2018, the contents of which are incorporated herein by reference in their entireties.

FIELD

The present general inventive concept relates to a compression bandage, and, more particularly, to a medical compression pad/bandage assembly to provide improved compression and wound care to a patient's suboccipital space.

BACKGROUND

It is known to provide bandages for a variety of medical purposes, including wound care of traumatically injured soft and hard tissues and following various medical procedures. Prior compression/bandage devices have been less than satisfactory in providing adjustable compression pads/bandages for suboccipital wound care which easily wraps around the head of the patient and which allows the patient to simply adjust compression and conform the pad to the anatomy of the patient to lessen the incidence of developing pseudomeningocele and cerebro-spinal fluid (CSF) lean and to enhance wound care following cranial surgery.

SUMMARY

According to various example embodiments of the present general inventive concept, a suboccipital compression pad that allows increased support and comfort through customizable fitting features and openings to prevent a patient's ears from being covered by the straps of the compression pad.

Additional aspects and advantages of the present general inventive concept will be set forth in part in the description which follows, and, in part, will be obvious from the description, or may be learned by practice of the present general inventive concept.

The foregoing and/or other aspects and advantages of the present general inventive concept may be achieved by providing a suboccipital compression pad including a pad member configured to contact an occipital region of a patient, and a pair of securing straps extending respectively from opposing ends of the pad member, at least one of the securing straps being provided with a fastening member at a distal end thereof and configured to fasten the at least one of the securing straps to the other securing strap proximate the forehead of the patient to compress the pad member to the occipital region, wherein each of the securing straps are configured with an open space such that portions of the respective securing straps are located above and below the patient's ears, without covering the ears, when the securing straps are fastened together.

The foregoing and/or other aspects and advantages of the present general inventive concept may also be achieved by providing a suboccipital compression pad assembly including a plurality of straps configured to wrap around the head of a patient, and a pad configured to compress against the patient's suboccipital region when first ends of the straps are fastened to one another proximate the patient's forehead.

In some aspects, the techniques described herein relate to a suboccipital compression pad, including: a pad member configured to contact a suboccipital region of a patient; and a pair of securing straps extending respectively from opposing ends of the pad member, the pair of securing straps having proximal ends diverging into upper rear straps and lower rear straps to form an open space between the upper rear straps and the lower rear straps such that portions of the upper rear straps are located above ears of the patient and portions of the lower rear straps are located below ears of the patient without covering ears of the patient; wherein one of the upper rear straps and the lower rear straps of the pair of securing straps is configured to be selectively attachable to different locations of a back side of the pad member.

In some aspects, the techniques described herein relate to a suboccipital compression pad, wherein both the upper rear straps and the lower rear straps of the pair of securing straps is configured to be selectively attachable to different locations of the back side of the pad member.

In some aspects, the techniques described herein relate to a suboccipital compression pad, wherein the upper rear straps and lower rear straps are configured with hook-and-loop fastening members so as to be selectively attachable to the back side of the pad member.

In some aspects, the techniques described herein relate to a suboccipital compression pad, wherein the upper rear straps and lower rear straps of one of the securing straps are longer than the upper and lower rear straps of the other of the securing straps.

In some aspects, the techniques described herein relate to a suboccipital compression pad, wherein the pad member includes a pouch configured to receive one or more compressive materials that are conformable to the occipital region.

In some aspects, the techniques described herein relate to a suboccipital compression pad, wherein the pouch is selectively sealable to contain the one or more compressive materials received therein.

In some aspects, the techniques described herein relate to a suboccipital compression pad, wherein the pad member includes a gel material that is conformable to the occipital region.

In some aspects, the techniques described herein relate to a suboccipital compression pad, wherein ends of the securing straps are fastened to one another proximate a forehead of the patient.

In some aspects, the techniques described herein relate to a suboccipital compression pad, wherein the upper rear straps and the lower rear straps are configured to bias the pad member towards one of a left-side and a right side of the occipital region of the patient.

In some aspects, the techniques described herein relate to a suboccipital compression pad, including: a pad member configured to contact a suboccipital region of a patient; and a pair of securing straps extending respectively from opposing ends of the pad member, the pair of securing straps having proximal ends diverging into upper rear straps and lower rear straps to form an open space between the upper rear straps and the lower rear straps such that portions of the upper rear straps are located above ears of the patient and portions of the lower rear straps are located below ears of the patient without covering ears of the patient; wherein one of the upper rear straps and the lower rear straps of the pair of securing straps is configured with hook-and-loop fastening members so as to be selectively attachable to different locations of a back side of the pad member.

In some aspects, the techniques described herein relate to a suboccipital compression pad, wherein both the upper rear straps and the lower rear straps of the pair of securing straps is configured to be selectively attachable to different locations of the back side of the pad member.

In some aspects, the techniques described herein relate to a suboccipital compression pad assembly, wherein the pad member is configured as a pouch to hold a predetermined amount of solidifier material.

In some aspects, the techniques described herein relate to a suboccipital compression pad, wherein the pouch is selectively sealable to contain the one or more compressive materials received therein.

In some aspects, the techniques described herein relate to a suboccipital compression pad, wherein the upper rear straps and lower rear straps of one of the securing straps are longer than the upper and lower rear straps of the other of the securing straps.

In some aspects, the techniques described herein relate to a suboccipital compression pad, wherein ends of the securing straps are fastened to one another proximate a forehead of the patient.

In some aspects, the techniques described herein relate to a suboccipital compression pad, including: a pad member configured to contact a suboccipital region of a patient; and a pair of securing straps extending respectively from opposing ends of the pad member, the pair of securing straps having proximal ends diverging into upper rear straps and lower rear straps to form an open space between the upper rear straps and the lower rear straps such that portions of the upper rear straps are located above ears of the patient and portions of the lower rear straps are located below ears of the patient without covering ears of the patient, wherein distal ends of the securing straps are fastened to one another proximate a forehead of the patient; wherein one of the upper rear straps and the lower rear straps of the pair of securing straps is configured to be selectively attachable to different locations of a back side of the pad member.

In some aspects, the techniques described herein relate to a suboccipital compression pad, wherein the upper rear straps and lower rear straps of one of the securing straps are longer than the upper and lower rear straps of the other of the securing straps.

In some aspects, the techniques described herein relate to a suboccipital compression pad assembly, wherein the pad member is configured as a pouch to hold a predetermined amount of solidifier material.

In some aspects, the techniques described herein relate to a suboccipital compression pad, wherein the pouch is selectively sealable to contain the one or more compressive materials received therein.

In some aspects, the techniques described herein relate to a suboccipital compression pad, wherein both the upper rear straps and the lower rear straps of the pair of securing straps is configured to be selectively attachable to different locations of the back side of the pad member.

Other features and aspects may be apparent from the following detailed description, the drawings, and the claims.

BRIEF DESCRIPTION OF THE DRAWINGS

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which.

DETAILED DESCRIPTION

Figure 1:
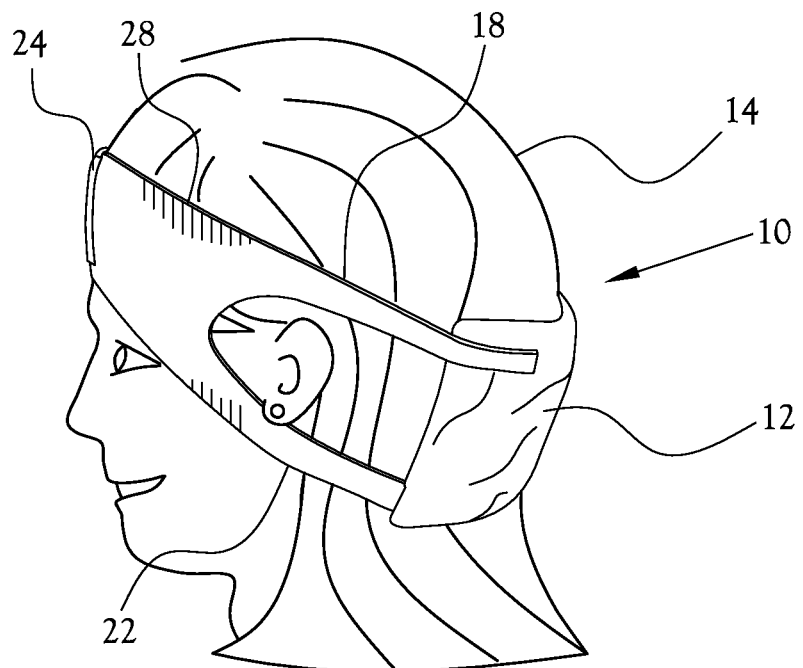
FIG. 1 illustrates a patient wearing a suboccipital compression pad according to an example embodiment of the present general inventive concept.

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

The following detailed description is provided to assist the reader in gaining a comprehensive understanding of the structures and fabrication techniques described herein. Accordingly, various changes, modification, and equivalents of the structures and fabrication techniques described herein will be suggested to those of ordinary skill in the art. The progression of fabrication operations described are merely examples, however, and the sequence type of operations is not limited to that set forth herein and may be changed as is known in the art, with the exception of operations necessarily occurring in a certain order. Also, description of well-known functions and constructions may be simplified and/or omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Aspects of the present disclosure provide a suboccipital compression pad which may be used by a patient following cranial surgery during the recuperation phase. In some example embodiments, the suboccipital compression pad assembly may have hook-and-loop fastener straps, such as VELCRO® straps, which can be adjusted to provide variable compression of the suboccipital region when the straps are wrapped around the patient's head. The suboccipital compression pad can be configured to conform to the patient's anatomy and the straps can be adjusted to wrap around the patient's ears and can fit multiple different ear sizes by adjusting the hook-and-loop fastener straps. Additionally, by adjusting the hook-and-loop fastener straps, the suboccipital compression pad can have a close fit around the patient's ears such that there is substantially full compression around the circumference of the patient's head in the affected area and such that only the ears of the patient remain exposed.

In some example embodiments, the suboccipital compression pad affixes, via the front hook-and-loop fastener straps to the patient's forehead. Many different patient head sizes may be accommodated for by adjusting the front hook-and-loop fastener straps. Thus, the suboccipital compression bandage can be easily removed by the patient in order to clean the affected area, change bandages, or to adjust the compression. Various example embodiments of the pad can be configured to accommodate multiple portions of the cranium to address the needs of various surgical procedures involving different parts of the patient's cranium.

The pad of the suboccipital compression pad may be configured in the shape of a pouch or envelope to contain gel or other compressive material which can conform to the anatomy of the patient's suboccipital region. The pouch can be filled with a solidifier powder and water may be added to create a malleable material to conform to the patient's anatomy. It is contemplated that the assembly can be configured as a kit to enable the patient to add a solidifier material and water sufficient to provide a predetermined amount of conformance and compression of the suboccipital space. The pouch can be configured to contain various types of gel material known and used in the medical/patient care industry to provide compressive support conformable to the patient's anatomy.

The suboccipital compression pad can be easily removed by the patient in order to clean the affected area, change bandages, or to adjust the compression. In some example embodiments, the patient may add a predetermined amount of powder and water sufficient to form a gel that is conformable to the patient's anatomy and of a sufficient weight to provide a desirable compression amount for comfortable and effective wound care.

The figures illustrate various examples of the suboccipital compression pad configured for use in accordance with example embodiments described herein.

Figure 2:
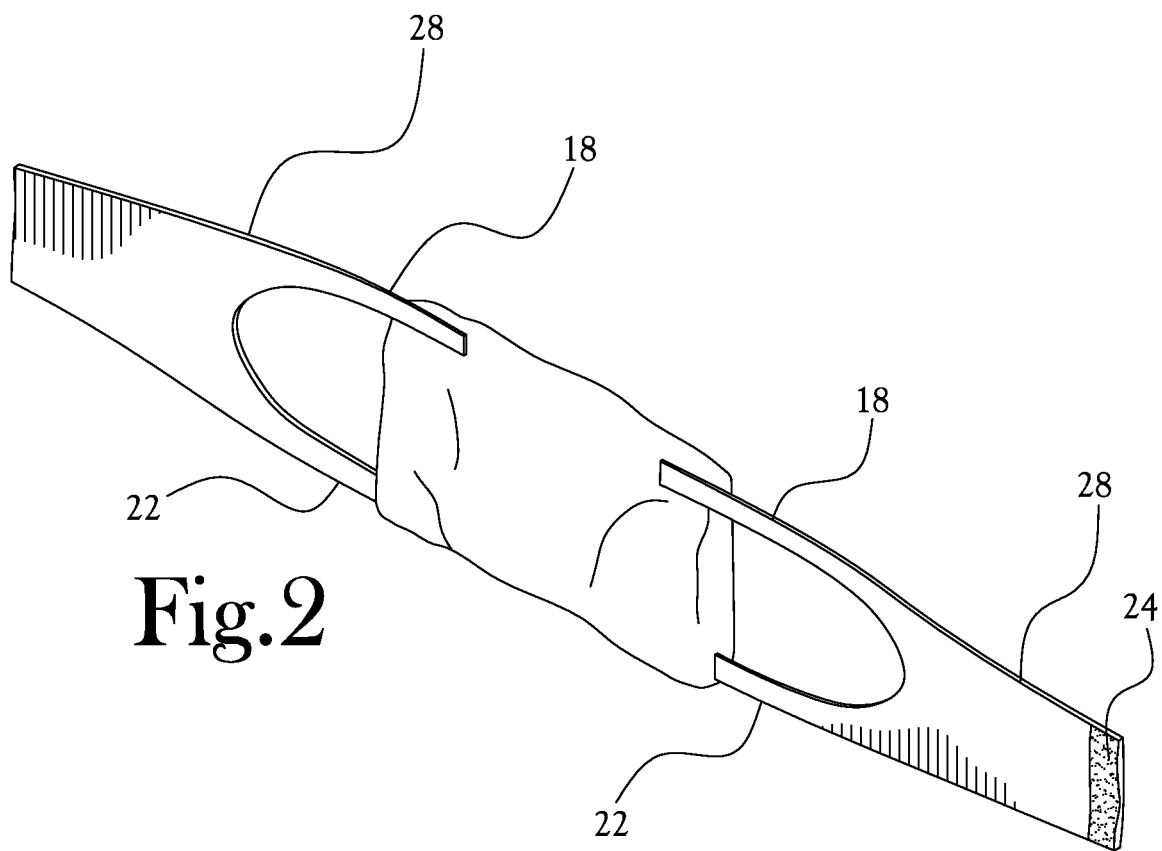
FIG. 2 illustrates a perspective view of the suboccipital compression pad of FIG. 1.

As illustrated in FIG. 1, the suboccipital compression pad 10 can be configured to wrap around the patient's head 14 and provide compression for the patient following cranial surgery. The suboccipital compression pad 10 diverges into two rear straps including upper rear straps 18 and lower rear straps 22 on each side of the patient's head 14 which can wrap around the patient's ears and can fit multiple different ear sizes by adjusting hook-and-loop attachment points on the straps. In the view shown in FIG. 1, the upper rear straps 18 can be configured to attach to a pad member 12 on the suboccipital compression pad 10, towards the rear of the patient's head 14 by means of hook-and-loop fastener straps, or other removable attachment devices known in the art, while the lower rear straps 22 can be fixedly attached to the pad member 12 of the suboccipital compression pad. In other embodiments, the lower rear straps 22 may also be removably attachable, to provide more adjustability to the patient. FIG. 2 illustrates a hook-and-loop attachment 24 on the front straps 28 of the suboccipital compression pad 10. While the rear straps 18,22 may be used to provide a close and comfortable fit around the patient's ears, the front straps 28 may be adjusted to provide sufficient, yet comfortable compression for the patient. Also shown in FIG. 1, at the rear of the suboccipital compression pad 10, is a pad member 12. The pad member 12 may contain various types of gel material known and used in the art to provide compressive support conformable to the patient's anatomy.

The pad member 12 may be a pouch used to hold a conformable gel material. In one aspect, the pad member 12 is a pouch filled with a solidifier powder and water, which may be added to hold fifty times the weight of the solidifier powder. The weight can be sufficient to provide a predetermined compression of the suboccipital space of the patient. The pad member 12 may be configured to contain various types of gel material known and used in the medical industry to provide compressive support conformable to the patient's anatomy.

Figure 3A:
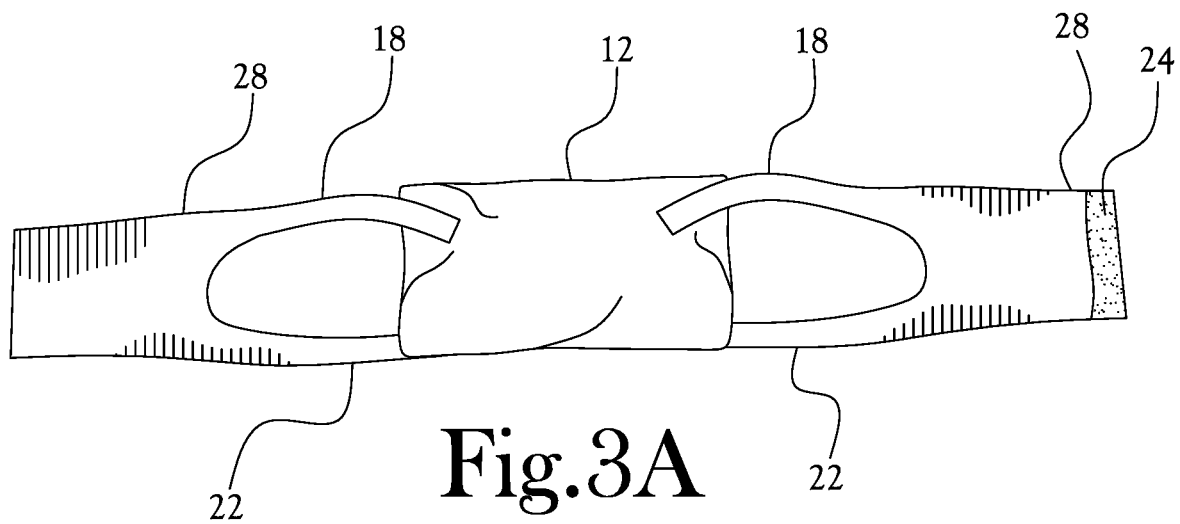
FIGS. 3A-B illustrate different selectable configurations of the suboccipital compression pad of FIG. 1.
Figure 3B:
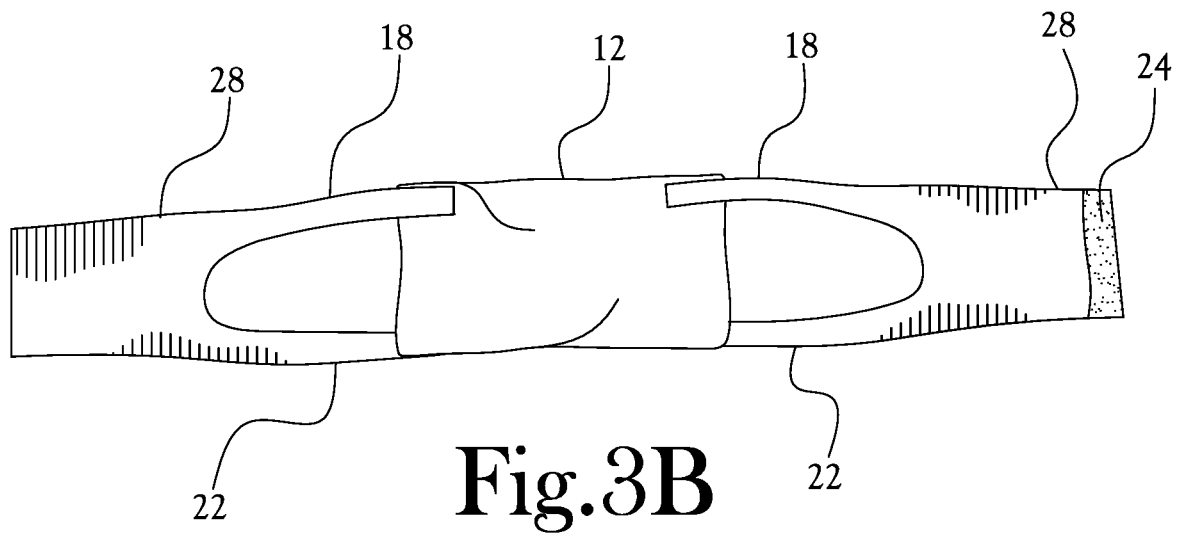

FIG. 3A shows an aspect of the suboccipital compression pad 10 with the upper rear straps 18 removably attached to the pad member 12 of the suboccipital compression pad 10. In this embodiment, the patient may be able to adjust the upper rear straps 18 to provide a closer fit around the ears of the patient and provide more compression. FIG. 3B shows the embodiment of FIG. 3A in which the upper rear straps 18 have been adjusted upward in relation to the lower rear straps 22.

In another aspect the lower rear straps 22 may be removably attached to the pouch of the suboccipital compression pad 10, and the upper rear straps 18 may be fixedly attached. In this embodiment, the patient can adjust the fit to provide for more comfort, while also providing a more secure attachment to the suboccipital compression pad. Other configurations are possible, for example where all the rear straps 18,22 are fixedly attached to the pad member 12 of the suboccipital compression pad.

Figure 4:
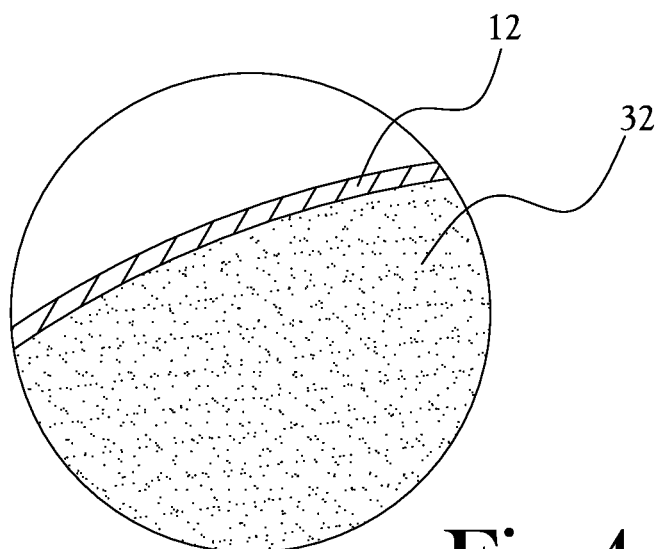
FIG. 4 illustrates a partial cross-section of the pad of a suboccipital compression pad according to an example embodiment of the present general inventive concept.
Figure 5A:
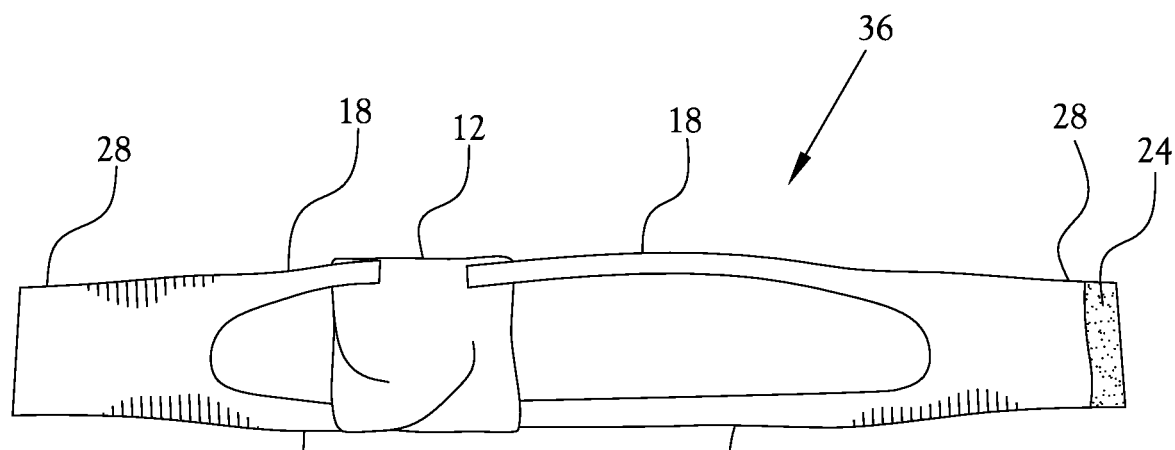
FIGS. 5A-B illustrate suboccipital compression pads according to two more example embodiments of the present general inventive concept.
Figure 5B:
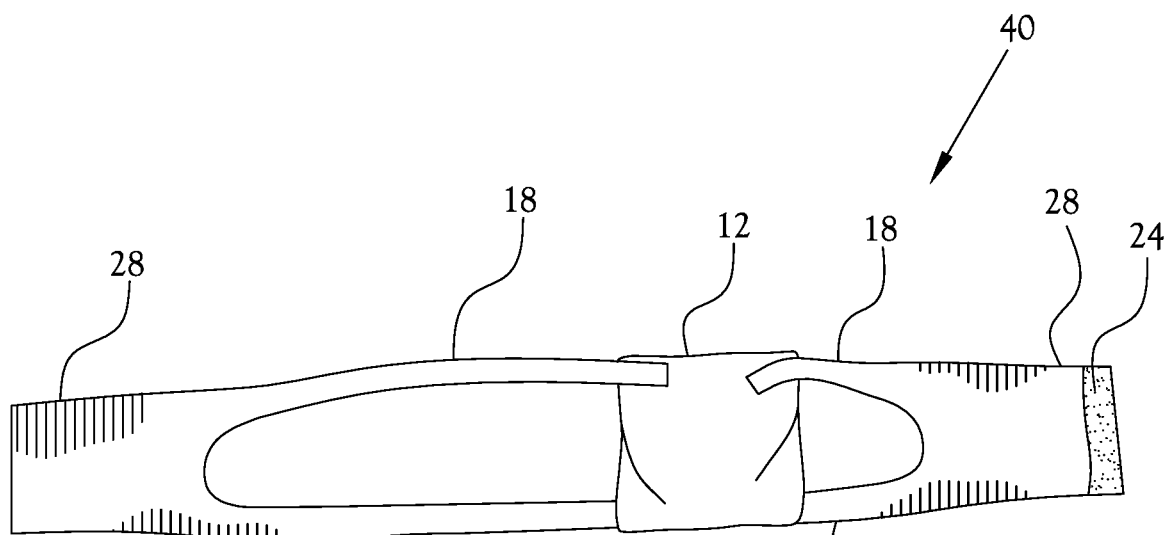

FIG. 4 shows a cross-sectional view of a portion of the pad member 12 of the suboccipital compression pad 10. In this embodiment the pad member 12 of the suboccipital compression pad 10 is filled with a pre-determined amount of gel 32 during the manufacturing process. FIG. 5A shows a left-side biased compression pad 36 applicable to variable compression on the left side of the suboccipital region of the patient's head 14, while FIG. 5B shows a right-side biased compression pad 40 applicable to variable compression on the right side of the suboccipital region of the patient's head 14.

Aspects of the suboccipital compression pad described herein may include a pad member configured to contact an occipital region of a patient, and a pair of securing straps extending respectively from opposing ends of the pad member, at least one of the securing straps being provided with a fastening member at a distal end thereof and configured to fasten the at least one of the securing straps to the other securing strap proximate the forehead of the patient to compress the pad member to the occipital region, wherein each of the securing straps are configured with an open space such that portions of the respective securing straps are located above and below the patient's ears, without covering the ears, when the securing straps are fastened together. Proximal ends of the securing straps may diverge into upper and lower rear straps to form the open space. The upper rear straps may be configured to be selectively attachable to different locations of a back side of the pad member. The upper rear straps may be configured with hook-and-loop fastening members so as to be selectively attachable to the back side of the pad member. The lower rear straps may be configured to be selectively attachable to different locations of the back side of the pad member. The upper and lower rear straps may be configured to be selectively attachable to different locations of the back side of the pad member. The upper and lower rear straps of one of the securing straps may be longer than the upper and lower rear straps of the other of the securing straps. The pad member may include a pouch configured to receive one or more compressive materials that are conformable to the occipital region. The pouch may be selectively sealable to contain the one or more compressive materials received therein. The pad member may include a gel material that is conformable to the occipital region.

Various examples of aspects described herein may provide a suboccipital compression pad assembly including a plurality of straps configured to wrap around the head of a patient, and a pad configured to compress against the patient's suboccipital region when first ends of the straps are fastened to one another proximate the patient's forehead. The pad may be configured as a pouch to hold a predetermined amount of solidifier material. The pouch may be attached to second ends of the straps such that the second ends can be selectively positioned relative to the pouch to adjust a position of the straps relative to the patient's ears. The first ends of the straps may be configured to be fastened to one another at various locations to adjust compression of the pad against the patient's suboccipital region.

Numerous variations, modifications, and additional embodiments are possible, and accordingly, all such variations, modifications, and embodiments are to be regarded as being within the spirit and scope of the present disclosure. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

It is noted that the simplified diagrams and drawings included in the present application do not illustrate all the various connections and assemblies of the various components, however, those skilled in the art will understand how to implement such connections and assemblies, based on the illustrated components, figures, and descriptions provided herein, using sound engineering judgment. Numerous variations, modification, and additional embodiments are possible, and, accordingly, all such variations, modifications, and embodiments are to be regarded as being within the spirit and scope of the present disclosure.

While aspects of the suboccipital compression pad 10 have been illustrated by description of several example embodiments, and while the illustrative embodiments have been described in detail, it is not the intention of the applicant to restrict or in any way limit the scope of aspects of the suboccipital compression pad 10 to such descriptions and illustrations. Instead, the descriptions, drawings, and claims herein are to be regarded as illustrative in nature, and not as restrictive, and additional embodiments will readily appear to those skilled in the art upon reading the above description and drawings. Additional modifications will readily appear to those skilled in the art. Accordingly, departures may be made from such details without departing from the spirit or scope of aspects disclosed herein.

What is claimed is:

1. A suboccipital compression pad, comprising:
a pad member configured to contact a suboccipital region of a patient; and
a pair of securing straps extending respectively from opposing ends of the pad member, the pair of securing straps having proximal ends diverging into upper rear straps and lower rear straps to form an open space between the upper rear straps and the lower rear straps such that portions of the upper rear straps are configured to be located above ears of the patient and portions of the lower rear straps are configured to be located below ears of the patient without covering ears of the patient;
wherein one of the upper rear straps and the lower rear straps of the pair of securing straps is configured to be selectively attachable to different locations of a back side of the pad member.

2. The suboccipital compression pad of claim 1, wherein both the upper rear straps and the lower rear straps of the pair of securing straps is configured to be selectively attachable to different locations of the back side of the pad member.

3. The suboccipital compression pad of claim 1, wherein the upper rear straps and lower rear straps are configured with hook-and-loop fastening members so as to be selectively attachable to the back side of the pad member.

4. The suboccipital compression pad of claim 1, wherein the upper rear straps and lower rear straps of one of the securing straps are longer than the upper and lower rear straps of the other of the securing straps.

5. The suboccipital compression pad of claim 1, wherein the pad member comprises a pouch configured to receive one or more compressive materials that are conformable to the suboccipital region.

6. The suboccipital compression pad of claim 5, wherein the pouch is selectively sealable to contain the one or more compressive materials received therein.

7. The suboccipital compression pad of claim 1, wherein the pad member comprises a gel material that is conformable to the suboccipital region.

8. The suboccipital compression pad of claim 1, wherein ends of the securing straps are configured to be fastened to one another proximate a forehead of the patient.

9. The suboccipital compression pad of claim 1, wherein the upper rear straps and the lower rear straps are configured to locate the pad member towards one of a left-side and a right side of the suboccipital region of the patient.

10. A suboccipital compression pad, comprising:
a pad member configured to contact a suboccipital region of a patient; and
a pair of securing straps extending respectively from opposing ends of the pad member, the pair of securing straps having proximal ends diverging into upper rear straps and lower rear straps to form an open space between the upper rear straps and the lower rear straps such that portions of the upper rear straps are configured to be located above ears of the patient and portions of the lower rear straps are configured to be located below ears of the patient without covering ears of the patient;
wherein one of the upper rear straps and the lower rear straps of the pair of securing straps is configured with hook-and-loop fastening members so as to be selectively attachable to different locations of a back side of the pad member.

11. The suboccipital compression pad of claim 10, wherein both the upper rear straps and the lower rear straps of the pair of securing straps is configured to be selectively attachable to different locations of the back side of the pad member.

12. The suboccipital compression pad of claim 10, wherein the pad member is configured as a pouch to hold a predetermined amount of solidifier material.

13. The suboccipital compression pad of claim 12, wherein the pouch is selectively sealable to contain one or more compressive materials received therein.

14. The suboccipital compression pad of claim 10, wherein the upper rear straps and lower rear straps of one of the securing straps are longer than the upper and lower rear straps of the other of the securing straps.

15. The suboccipital compression pad of claim 10, wherein ends of the securing straps are configured to be fastened to one another proximate a forehead of the patient.

16. A suboccipital compression pad, comprising:
  a pad member configured to contact a suboccipital region of a patient; and
  a pair of securing straps extending respectively from opposing ends of the pad member, the pair of securing straps having proximal ends diverging into upper rear straps and lower rear straps to form an open space between the upper rear straps and the lower rear straps such that portions of the upper rear straps are configured to be located above ears of the patient and portions of the lower rear straps are configured to be located below ears of the patient without covering ears of the patient, wherein distal ends of the securing straps are configured to be fastened to one another proximate a forehead of the patient;
  wherein one of the upper rear straps and the lower rear straps of the pair of securing straps is configured to be selectively attachable to different locations of a back side of the pad member.

17. The suboccipital compression pad of claim 16, wherein the upper rear straps and lower rear straps of one of the securing straps are longer than the upper and lower rear straps of the other of the securing straps.

18. The suboccipital compression pad of claim 16, wherein the pad member is configured as a pouch to hold a predetermined amount of solidifier material.

19. The suboccipital compression pad of claim 18, wherein the pouch is selectively sealable to contain one or more compressive materials received therein.

20. The suboccipital compression pad of claim 16, wherein both the upper rear straps and the lower rear straps of the pair of securing straps is configured to be selectively attachable to different locations of the back side of the pad member.

* * * * *